(12) United States Patent
Hahl et al.

(10) Patent No.: US 11,217,397 B2
(45) Date of Patent: Jan. 4, 2022

(54) SEGMENTED CONFORMAL ANODE FOR A CAPACITOR

(71) Applicant: Greatbatch, Ltd., Clarence, NY (US)

(72) Inventors: Jason T. Hahl, East Aurora, NY (US); Barry C. Muffoletto, Alden, NY (US); Anthony C Perez, Wheatfield, NY (US); Christina Scheuer, Amherst, NY (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 17/151,258

(22) Filed: Jan. 18, 2021

(65) Prior Publication Data

US 2021/0220652 A1    Jul. 22, 2021

Related U.S. Application Data

(60) Provisional application No. 62/962,403, filed on Jan. 17, 2020.

(51) Int. Cl.
*H01G 9/052* (2006.01)
*H01G 9/145* (2006.01)
*H01G 9/008* (2006.01)

(52) U.S. Cl.
CPC ............ *H01G 9/052* (2013.01); *H01G 9/008* (2013.01); *H01G 9/145* (2013.01)

(58) Field of Classification Search
CPC ......... H01G 9/052; H01G 9/008; H01G 9/145
See application file for complete search history.

(56) References Cited

U.S. PATENT DOCUMENTS

| | | |
|---|---|---|
| 5,894,403 A | 4/1999 | Shah et al. |
| 5,920,455 A | 7/1999 | Shah et al. |

(Continued)

FOREIGN PATENT DOCUMENTS

JP   2004247410 A  *  9/2004  ............ H01G 9/012

OTHER PUBLICATIONS

"European Search Report, Application No. 21152177.8 dated Jun. 21, 2021".

(Continued)

*Primary Examiner* — Eric W Thomas
(74) *Attorney, Agent, or Firm* — Michael F. Scalise

(57) ABSTRACT

A capacitor for powering an implantable medical device is described. The capacitor includes a casing having contoured surfaces to more closely conform to body contours. This means that the anode housed in the casing must also have a contoured shape substantially matching that of the casing. Accordingly, the anode is comprised of a pressed pellet having a surrounding peripheral edge extending to spaced-apart first and second major face walls. An anode lead wire comprises an embedded portion extending into the anode pellet. First and second channel-shaped recesses aligned with each other extend into the anode pellet from the first and second major face walls to intersect with the embedded lead wire portion. The first and second channel-shaped recesses also extend to opposed locations at the surrounding peripheral edge of the anode pellet. The anode pellet is bent at the aligned first and second channel-shaped recesses to provide a right anode pellet portion electrically connected to a left anode pellet portion by the embedded lead wire portion. The thusly contoured anode pellet has an anatomical shape that matches that of the contoured casing to provide an implantable capacitor that is volumetrically efficient.

20 Claims, 8 Drawing Sheets

(56) References Cited

U.S. PATENT DOCUMENTS

| | | | |
|---|---|---|---|
| 5,949,639 A | 9/1999 | Maeda et al. | |
| 6,219,222 B1 | 4/2001 | Shah et al. | |
| 6,224,985 B1 | 5/2001 | Shah et al. | |
| 6,468,605 B2 | 10/2002 | Shah et al. | |
| 6,599,580 B2 | 7/2003 | Muffoletto et al. | |
| 6,687,117 B2 | 2/2004 | Liu et al. | |
| 7,116,547 B2 | 10/2006 | Seitz et al. | |
| 7,154,742 B1 * | 12/2006 | Hahn | H01G 9/048 361/528 |
| 7,813,107 B1 * | 10/2010 | Druding | H01G 9/008 361/508 |
| 9,312,075 B1 | 4/2016 | Liu et al. | |
| 9,633,796 B2 | 4/2017 | Liu et al. | |
| 9,721,730 B1 * | 8/2017 | Muffoletto | H01G 9/14 |
| RE47,435 E | 6/2019 | Shah et al. | |
| RE47,560 E | 8/2019 | Liu et al. | |

OTHER PUBLICATIONS

"Extended European Search Report, Application No. 21152177.8 dated Sep. 23, 2021".

* cited by examiner

SEGMENTED CONFORMAL ANODE FOR A CAPACITOR

CROSS-REFERENCE TO RELATED APPLICATION

This application claims priority to U.S. provisional patent application Ser. No. 62/962,403, filed on Jan. 17, 2020.

BACKGROUND OF THE INVENTION

The present invention generally relates to a capacitor and, more particularly, to a capacitor capable of powering an implantable medical device, such as a cardiac defibrillator.

More specifically, the present invention relates to casings for implantable capacitors, the capacitors being particularly adapted for powering implantable medical devices. Accordingly, the casings have contoured surfaces to more closely conform to body contours. This means that the anode housed in the casing must also have a contoured shape substantially matching that of the casing. Capacitors with contoured casings facilitate implantation in areas of a body that were heretofore not possible because of geometrical limitations.

SUMMARY OF THE INVENTION

In general, an electrochemical/electrolytic hybrid or an electrolytic capacitor consists of an anode and a cathode that are separated from each other by an ionically conductive working electrolyte or a porous separator impregnated with a working electrolyte. The anode is made of a valve metal, such as tantalum, aluminum, niobium, or titanium, that has been pressed into a shaped pellet and sintered at a relatively high temperature for a period that is sufficient to coalesce the pressed valve metal material into a cohesive body. The sintered valve metal pellet is then anodized in an anodizing electrolyte to form a film of the corresponding oxide serving as a dielectric on the valve metal. The final anodizing voltage determines the dielectric oxide film thickness, which relates to the rated capacity of the thusly formed anode.

These and other aspects of the present invention will become more apparent to those skilled in the art by reference to the following description and to the appended drawings.

DETAILED DESCRIPTION OF THE PREFERRED EMBODIMENTS

In the present invention, the valve metal powder, preferably tantalum, is molded under pressure to form a pellet having a desired shape. A lead wire is embedded in the powder before pressing or is welded to the subsequent pellet. For either an electrolytic or a hybrid capacitor, the tantalum anode is preferably in the form of a pressed/sintered tantalum powder pellet. Beam melt, sodium reduction, or other processes produce the tantalum powders. Exemplary beam melt and sodium reduced tantalum powders are available from Taniobis GmbH, Goslar, Germany under the "QR" and "NH" family designations, respectively. Tantalum powder from Taniobis GmbH under the "HV" designation is also useful with the present invention.

Further, U.S. Pat. Nos. 9,312,075, 9,633,796 and Re47,560, all to Liu et al. and assigned to the assignee of the present invention, describe improved tantalum powders that are suitable for making a tantalum pellet. When pressed into a pellet and then sintered, the tantalum pellet has defined inter-granule and intra-granule pore size distributions attributed to its sintered density that make the material particularly well-suited for use in an electrolytic capacitor.

Figure 1A:
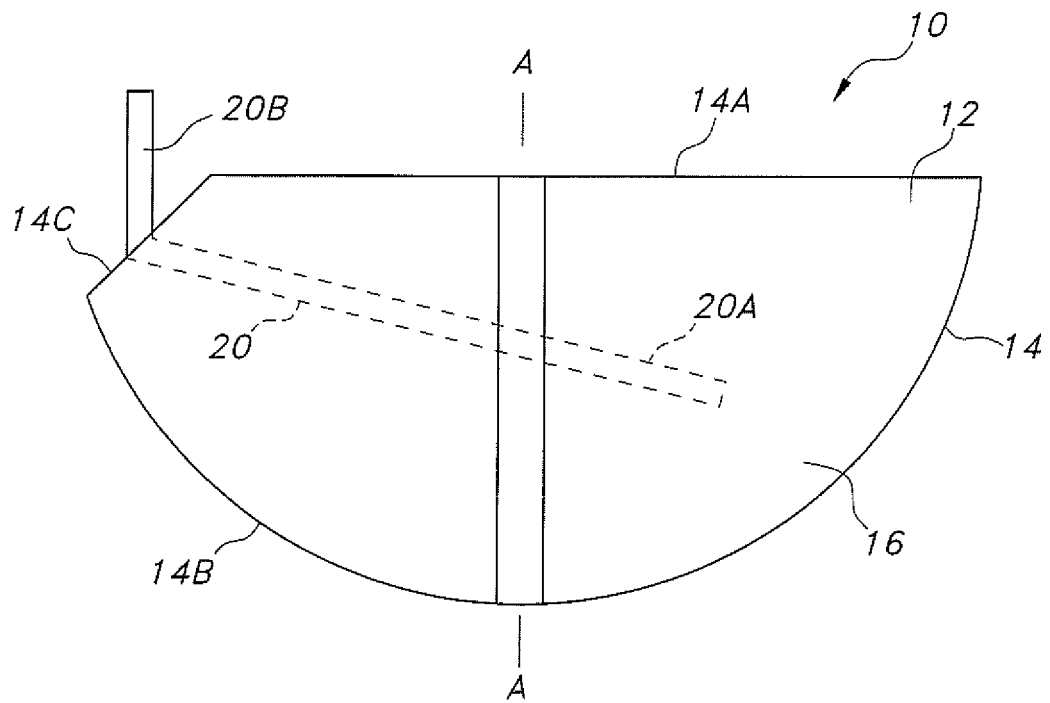
FIG. 1A is a side elevational view of an anode 10 according to the present invention.
Figure 1B:
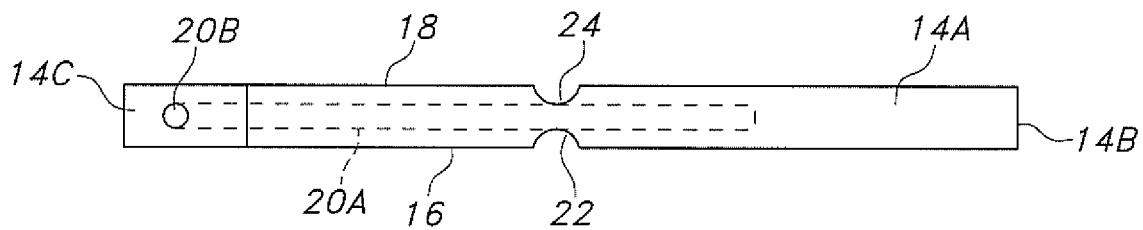
FIG. 1B is a plan view looking down at the upper edge 14A and 14C of the anode 10 shown in FIG. 1.

Referring now to the drawings, FIGS. 1A and 1B illustrate one embodiment of an anode 10 according to the present invention. The anode 10 is comprised of a pressed pellet 12 of a valve metal, for example, of tantalum and has a thickness defined by a surrounding edge wall 14 extending to a first or front major face wall 16 spaced from and opposed to a second or back major face wall 18. The surrounding edge wall 14 has an upper edge portion 14A meeting a curved bottom edge portion 14B. The upper and bottom edge portions 14A, 14B extend to and meet with the opposite ends of a substantially planar left edge portion 14C. The planar left edge portion 14C is angled with respect to the upper edge portion 14A.

An anode lead wire 20 has an embedded lead wire portion 20A that extends into the anode pellet 12, generally centered between the front and back major face walls 16, 18. The embedded lead wire portion 20A is integrally connected to an extending lead wire portion 20B that extends outwardly from the left edge portion 14C of the surrounding edge wall 14.

FIG. 1A illustrates that a first U-shaped channel recess 22 extends inwardly from the front major face wall 16 part-way into the thickness of the anode edge wall 14. The U-shaped channel recess 22 has a length extending along a longitudinal axis A-A from the upper edge portion 14A to the curved bottom edge portion 14B of the surrounding edge wall. In the drawing, the longitudinal axis A-A of the U-shaped channel recess 22 intersects the embedded lead wire portion 20A and is aligned perpendicular to the upper edge portion 14A. Other embodiments of an anode according to the present invention have the U-shaped channel recess 22 intersecting the embedded lead wire portion 20A but aligned at an angle that is other than perpendicular the planar upper edge portion 14A of the surrounding edge wall 14.

FIG. 1B further illustrates that a second U-shaped channel recess 24 extends inwardly from the back wall 18, part-way into the thickness of the surrounding edge wall 14. In a similar manner as with the first U-shaped channel recess 22, the second channel recess 24 intersects the embedded lead wire portion 20A and is aligned perpendicular to the upper edge portion 14A of the surrounding sidewall 14. Again, other embodiments of an anode according to the present invention have the longitudinal axis of the second U-shaped channel recess 24 intersecting the embedded lead wire portion 20A but aligned at an angle that is other than perpendicular with respect to the upper edge portion 14A. In addition to each of the first and second U-shaped channel recesses 22, 24 extending inwardly part-way into the thickness of the anode to intersect the embedded lead wire portion 20A, it is important that they are aligned front-to-back with each other. Aligning the first and second channel recesses 22 and 24 front-to-back with each other enables the anode 10 to be bent into a configuration exemplified by that shown in FIG. 2.

Figure 2:
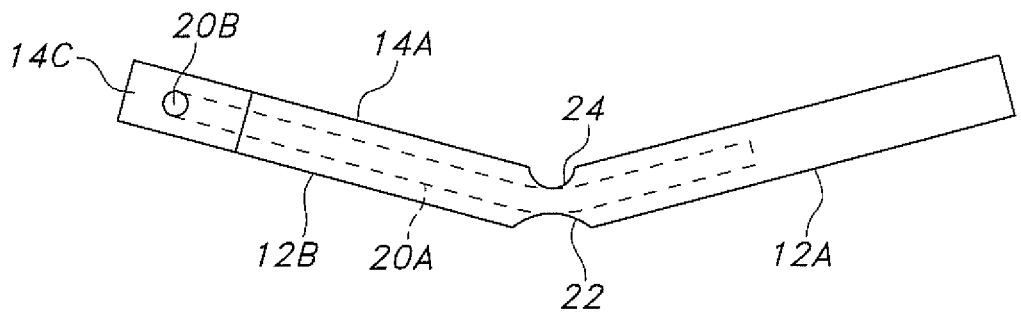
FIG. 2 is a plan view of the anode 10 shown in FIGS. 1 and 1A after having been bent along opposed channel-shaped recesses 22 and 24.

FIG. 2 is a plan view looking down at the upper and left edge portions 14A, 14C of the surrounding edge wall 14. The anode is bent at the embedded lead wire portion 20A and the aligned U-shaped channel recesses 22 and 24 so that the anode pellet 12 conforms to the shape of a contoured casing, as will be described in detail hereinafter. In its bent configuration, the anode pellet 12 has a right pellet portion 12A that is at an acute angle with respect to a left pellet portion 12B. The bent embedded lead wire portion 20A keeps the right and left pellet portions 12A, 12B connected to each other and ensures that there is electrical continuity from the right pellet portion 12A to the left pellet portion 12B and then to the extending lead wire portion 20B.

Figure 3:
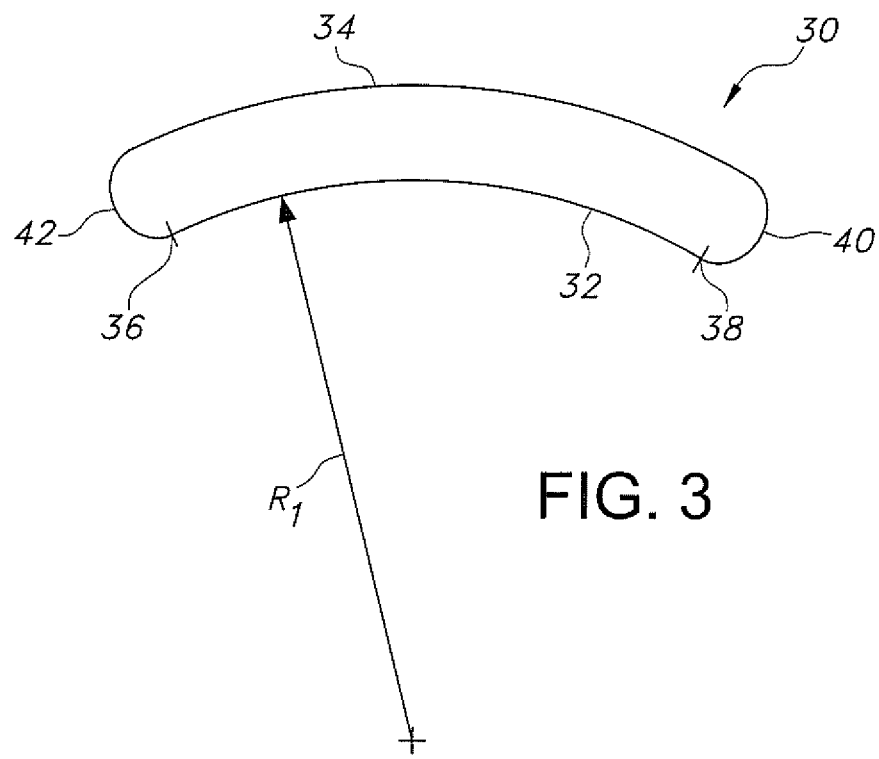
FIG. 3 is a schematic, cross-sectional view of a casing 30 having opposed major curved side walls of a radius $R_1$.
Figure 4:
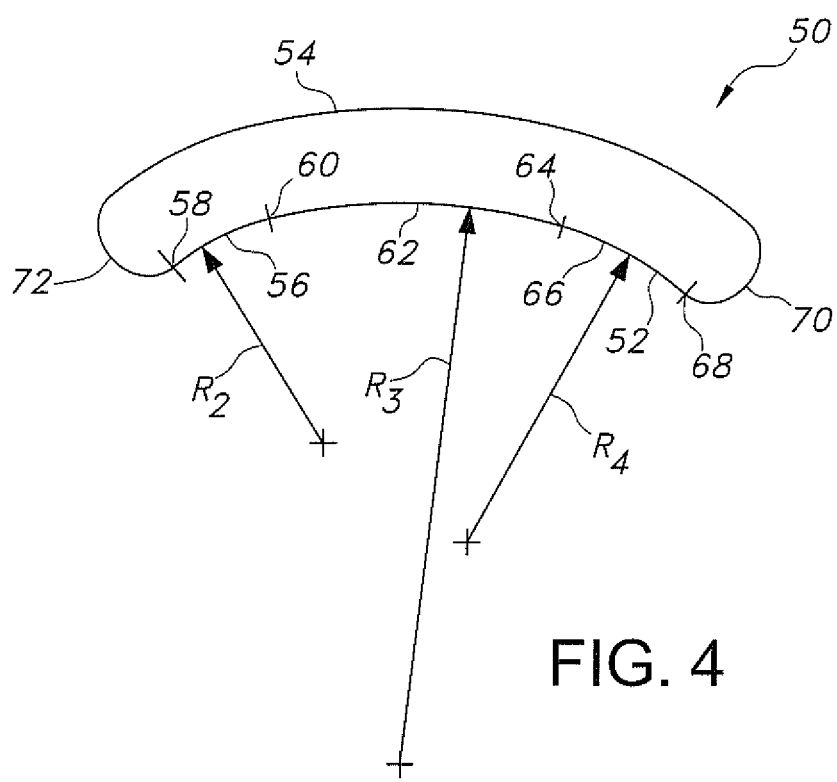
FIG. 4 is a schematic, cross-sectional view of a casing 50 having opposed major curved side walls of varying radii $R_2$ to $R_4$.
Figure 5:
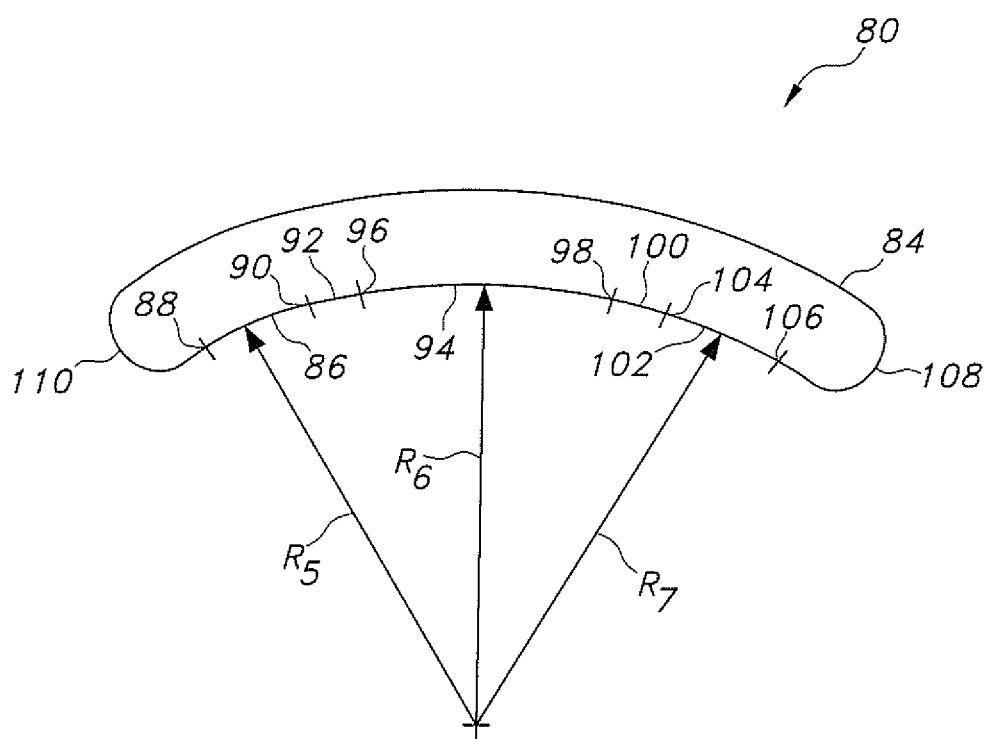
FIG. 5 is a schematic, cross-sectional view of a casing 80 having opposed major curved side walls of varying radii $R_5$ to $R_6$ with intermediate planar sections.

Referring now to FIGS. 3 to 5, representative schematic cross-sectional views of casings that are suitable for housing the anode 10 shown in FIGS. 1, 1A and 2 are illustrated. In general, the casings have contoured or curved opposed major sidewalls that align with the bent contour of the right and left anode pellet portions 12A, 12B.

In FIG. 3, the casing 30 comprises spaced apart and opposed major first and second sidewalls 32 and 34, each of a curvature defined by the radius $R_1$ moving along a path from tangent point 36 to tangent point 38. The radius $R_1$ is not shown for the second sidewall 34, however, it is the same as that of the first sidewall 32. The sidewalls 32, 34 extend to curved end walls 40 and 42 and a bottom wall (not shown). As will be described in detail hereinafter, the casing 30 is closed by a lid (not shown).

FIG. 4 shows another embodiment of a casing 50 comprising spaced apart and opposed major first and second curved sidewalls 52 and 54. The first major sidewall 52 is comprised of a first curved portion 56 defined by radius $R_2$ moving along a path from tangent point 58 to tangent point 60 where the sidewall transitions to a second curved portion 62 defined by radius $R_3$ moving along a path from tangent point 60 to tangent point 64. At tangent point 64, the second curved portion 62 transitions to a third curved portion 66 defined by radius $R_4$ moving along a path from tangent point 64 to tangent point 68.

As FIG. 4 shows, the length of the radius $R_2$ is less than that of both $R_3$ and $R_4$ while the length of radius $R_4$ is less than that of $R_3$. The second major sidewall 54 is similar in its contoured or curved shape. The sidewalls 52 and 54 extend to curved end walls 70 and 72 and a bottom wall (not shown). The casing 50 is then closed by a lid (not shown).

It is within the scope of the present invention that the arrangement of the respective curved portions 56, 62 and 66 can be rearranged in any sequence or manner. Also, there can be only two different curved portions in a sidewall or more than three. The exact number and their arrangement is only limited by the application in which the capacitor will be used.

FIG. 5 shows another embodiment of a casing 80 comprising spaced apart and opposed major first and second curved sidewalls 82 and 84 according to the present invention. The first major sidewall 82 is comprised of a first curved portion 86 defined by radius $R_5$ moving along a path from tangent point 88 to tangent point 90 where the sidewall transitions to a first planar or straight portion 92. The first planar portion 92 then transitions to a second curved portion 94 defined by radius $R_6$ moving along a path from tangent point 96 to tangent point 98. At tangent point 98, the sidewall 82 transitions to a second planar portion 100 which, in turn, transitions to a third curved portion 102 defined by radius $R_7$ moving along a path from tangent point 104 to tangent point 106.

As the drawing shows, the lengths of radii $R_5$, $R_6$ and $R_7$ are equal. However, as described above with respect to FIG. 4, that is not necessary. The lengths of planar portions 92 and 102 are equal, however, that is also not necessary. There can be more than or less than two planar portions in a sidewall and they can be continuous and angled with respect to each other or separated from each other by one or more curved portions.

Again, the second major sidewall 84 is similar in shape to the first sidewall 82. The sidewalls 82 and 84 extend to curved end walls 108 and 110 and a bottom wall (now shown). The casing 80 is then closed by a lid (not shown).

Figure 6:
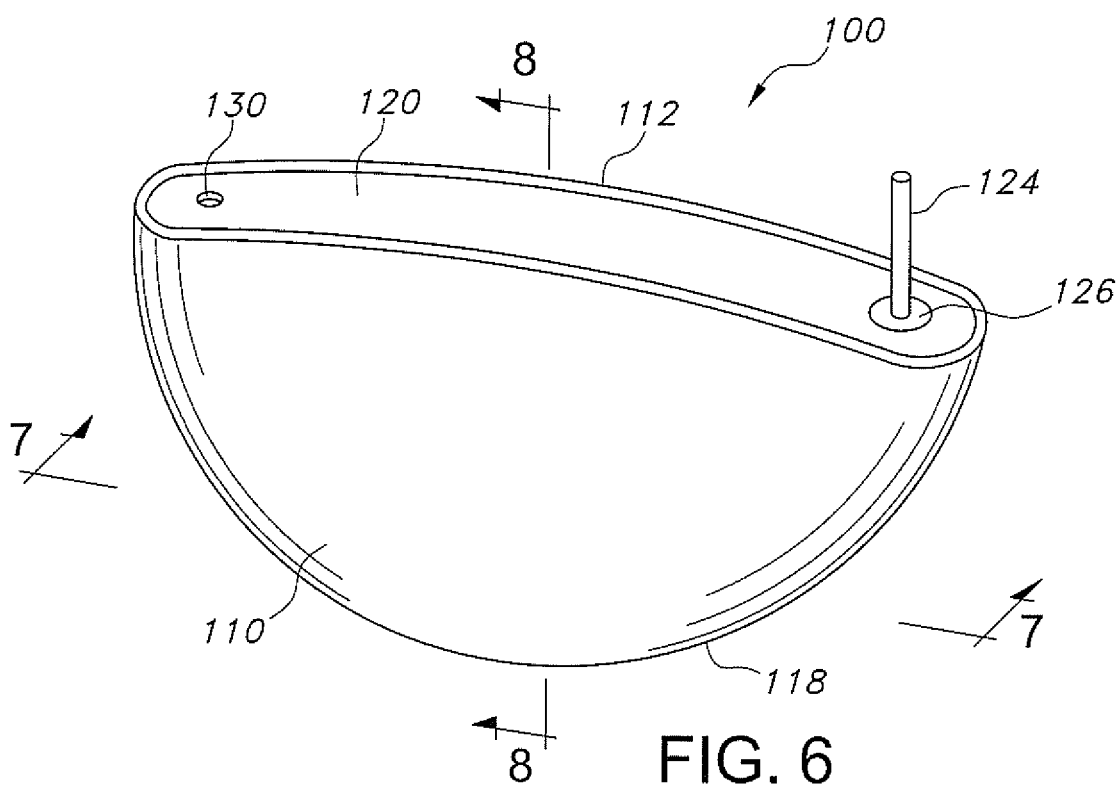
FIG. 6 is a side-elevational view of a capacitor 100 according to the present invention.
Figure 7:
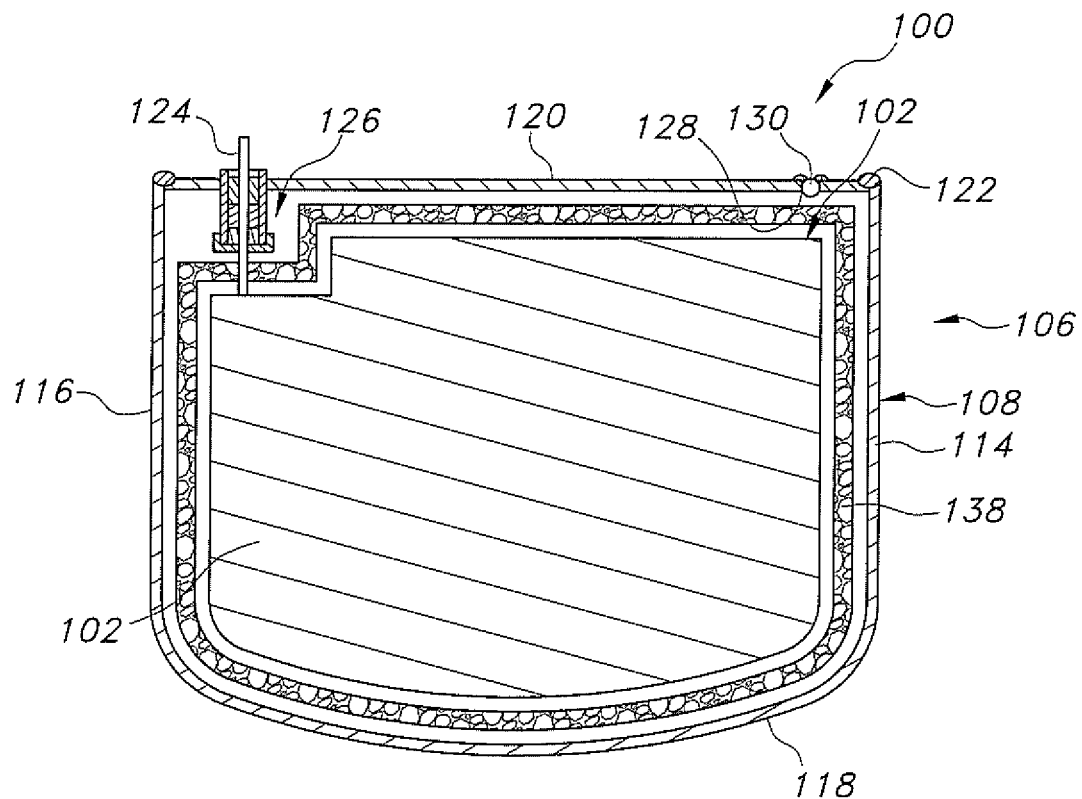
FIG. 7 is a cross-sectional view taken along line 7-7 of the capacitor 100 shown in FIG. 6.
Figure 8:
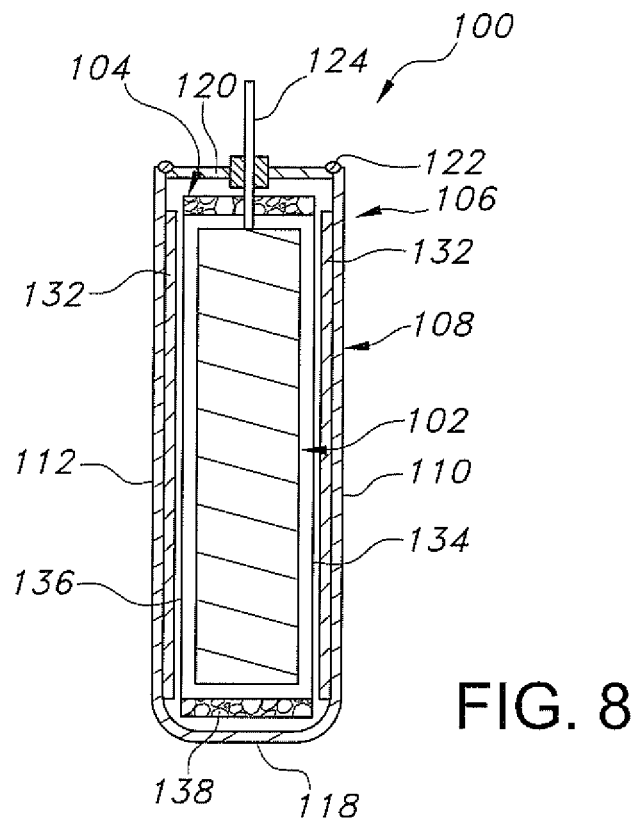
FIG. 8 is a cross-sectional view taken along line 8-8 of the capacitor 100 shown in FIG. 6.

Referring now to FIGS. 6 to 8, an exemplary capacitor 100 according to the present invention is shown. Capacitor 100 comprises an anode 102 and a cathode 104 housed inside of a hermetically sealed contoured casing 106. The capacitor electrodes are contacted by a working electrolyte (not shown) contained inside the casing 106, as will be described in detail hereinafter. The capacitor 100 can be of either an electrochemical type where both the anode and the cathode are provided by conductive substrates having a capacitive material contacted thereto or, of an electrolytic type where the cathode is provided by a conductive substrate having capacitive properties. The exemplary capacitor 100 illustrated in FIGS. 6 to 8 is of the latter type, however, that should not be construed as limiting.

Casing 106 includes a container 108 having a contoured shape comprised of spaced apart curved sidewalls 110 and 112 extending to and meeting with opposed curved end walls 114 and 116 extending from a curved bottom wall 118. The curved sidewalls 110 and 112 are contoured according to a desired one of the various casing sidewall shapes described above with respect to FIGS. 3 to 5. A lid 120 is secured to the sidewalls 110, 112 and the end walls 114, 116 by a weld 122 to close the container 108 and thereby provide the casing 106. Casing 106 is of a conductive metal and as such serves as one terminal or contact for making electrical connection between the capacitor and its load. The weld 122 is provided by any conventional means; however, a preferred method is by laser welding.

The other electrical terminal or contact for the capacitor 100 is provided by a conductor or lead wire 124 extending from within the casing 106 and more particularly through the lid 120. Lead wire 124 is insulated electrically from the metal lid 120 by an insulator and seal structure 126 commonly referred to as a glass-to-metal seal. An electrolyte fill opening 128 in lid 120 is sealed by a closure structure 130. Preferably, the closure structure 130 is welded to the casing 106 to close the opening 128.

The cathode 104 is spaced from the anode 102 housed inside the casing and comprises an electrode active material 132 provided on a conductive substrate. The active material has a thickness of about a few hundred Angstroms to about 0.1 millimeters. When the casing 106 serves as one terminal or contact for the capacitor, the container 108 serves as the conductive substrate or, the conductive substrate provided with the active material 132 is electrically connected to the container 108. In either case, the casing or conductive substrate is selected from the group consisting of tantalum, titanium, nickel, molybdenum, niobium, cobalt, stainless steel, tungsten, platinum, palladium, gold, silver, copper, chromium, vanadium, aluminum, zirconium, hafnium, zinc and iron, and mixtures and alloys thereof. The lid 120 is also preferably of one of the above conductive materials. Preferably the conductive substrate has a thickness of about 0.001 to 2 millimeters.

Preferably, the conductive substrate is cleaned of contaminants from handling equipment, body oils from hands, and the like, and roughened by chemical or mechanical means to increase its surface area prior to being contacted with the active material 132. If desired, the electrical conductivity of the uncoated substrate can be improved by a technique described in U.S. Pat. No. 6,599,580 to Muffoletto et al., which is assigned to the assignee of the present invention and incorporated herein by reference.

After preparation, the active material 132 is contacted to the conductive substrate preferably after, but possibly before, the prepared substrate is cut, shaped or otherwise fabricated into the desired geometry. To provide a capacitor electrode, the substrate may be of an anodized-etched conductive material, have a sintered active material with or without oxide contacted thereto, be contacted with a double layer capacitive material, for example a finely divided carbonaceous material such as graphite or carbon or platinum black, a redox, pseudocapacitive or an under potential material, or an electroactive conducting polymer such as polyaniline, polypyrrole, polythiophene and polyacetylene, and mixtures thereof. The capacitive material is preferably contacted to the conductive substrate using the pad printing process described in U.S. Pat. No. 7,116,547 to Seitz et al., which is assigned to the assignee of the present invention and incorporated herein by reference. Another method is as an ultrasonically generated aerosol of the conductive material coating the interior surfaces of the container 108. In either case, FIGS. 6 to 8 illustrate that most of sidewalls 110 and 112 are provided with the electrode active material 132. Other configurations of active material contacted to the conductive sidewalls are contemplated by the scope of the present invention as needed for a specific application.

According to one preferred aspect of the present invention, the electrode active material 132 includes an oxide of a metal, the nitride of a metal, the carbon nitride of a metal, or the carbide of a metal, and mixture thereof, the oxide, nitride, carbon nitride and carbide of the metal having pseudocapacitive properties. The metal is preferably selected from the group of ruthenium, cobalt, manganese, molybdenum, tungsten, tantalum, iron, niobium, iridium, titanium, zirconium, hafnium, rhodium, vanadium, osmium, palladium, platinum, nickel, lead, and mixtures thereof. In a preferred embodiment of the invention, the electrode active material 132 includes an oxide of ruthenium or oxides of ruthenium and tantalum.

In accordance with one embodiment of the present invention, the fabricated container 108 is provided with the active material 132 deposited on the sidewalls 110 and 112 of the container 108 (FIG. 6) serving as the conductive substrate. Alternatively, a conductive substrate of one of the enumerated materials is first provided with the electrode active material 132 coating and the thusly processed substrate is then contacted to the casing sidewalls 110 and 112. As previously discussed, the processed conductive substrate can provide the anode and/or the cathode in an electrochemical capacitor, or the cathode in an electrolytic capacitor. The exemplary capacitor shown in FIGS. 6 to 8 is of the electrolytic type and the cathode active material preferably coats the sidewalls beginning at a position spaced from the bottom wall of the container 108 to a distance spaced from the lid 120. Such a coating is accomplished by providing the conductive substrate with a masking material in a known manner so that only the intended area of the substrate is contacted with active material. The masking material is then removed from the substrate prior to capacitor fabrication. Preferably, the cathode active material is substantially aligned in a face-to-face relationship with the major surfaces of the anode 102.

Suitable coating processes are described in U.S. Pat. No. 5,894,403 to Shah et al., U.S. Pat. No. 5,920,455 to Shah et al., U.S. Pat. No. 6,224,985 to Shah et al. and U.S. Pat. No. 6,468,605 to Shah et al. These patents are assigned to the assignee of the present invention and incorporated herein by reference. In that manner, the ultrasonically generated active material contacted to the conductive substrate has most of its particles with diameters of less than about 10 microns. This provides an internal surface area for the active material of about 10 $m^2$/gram to about 1,500 $m^2$/gram.

The anode 102 is typically of a metal selected from the group of tantalum, aluminum, titanium, niobium, zirconium, hafnium, tungsten, molybdenum, vanadium, silicon, germanium, and mixtures thereof, and is in the form of a pellet. As is well known by those skilled in the art, the anode metal in powdered form, for example tantalum powder, is compressed into a pellet having a lead wire 124 extending therefrom. The anode pellet including the lead wire 124 are sintered under a vacuum at high temperatures. The porous body is then anodized in a suitable anodizing electrolyte to fill the pores between adjacent tantalum particles with the electrolyte and form a continuous dielectric oxide film on the sintered body. The assembly is then reformed to a desired voltage, as is well known by those skilled in the art, to produce an oxide layer over the terminal lead wire 124 and, if the lead wire is welded to the anode, the anode lead wire weld. The anode 102 can also be of an etched aluminum or titanium foil or, a sintered aluminum or titanium body.

A separator structure of electrically insulative material is provided between the anode 102 and the cathode 104 to prevent an internal electrical short circuit between the electrodes. The separator also is chemically unreactive with the anode and cathode active materials and both chemically unreactive with and insoluble in the working electrolyte. In addition, the separator has a degree of porosity sufficient to allow flow therethrough of the working electrolyte during the electrochemical reaction of the capacitor 100. Illustrative separator materials include woven and non-woven fabrics of polyolefinic fibers including polypropylene and polyethylene or fluoropolymeric fibers including polyvinylidene fluoride, polyethylenetetrafluoroethylene, and polyethylenechlorotrifluoroethylene laminated or superposed with a polyolefinic or fluoropolymeric microporous film, non-woven glass, glass fiber materials and ceramic materials. Suitable microporous films include a polyethylene membrane commercially available under the designation SOLUPOR (DMS Solutech), a polytetrafluoroethylene membrane commercially available under the designation ZITEX (Chemplast Inc.), a polypropylene membrane commercially available under the designation CELGARD (Celanese Plastic Company, Inc.) and a membrane commercially available under the designation DEXIGLAS (C. H. Dexter, Div., Dexter Corp.). Cellulose based separators typically used in capacitors are also contemplated by the scope of the present invention. Depending on the working electrolyte, the separator can be treated to improve its wettability, as is well known by those skilled in the art.

Suitable working electrolytes are described in Reissue Pat. No. RE47,435, which relates to U.S. Pat. No. 6,219,222 to Shah et al. and Reissue application Ser. No. 14/534,357, which relates to U.S. Pat. No. 6,687,117 to Liu et al.

FIGS. 6 to 8 illustrate one embodiment of a separator structure according to the present invention wherein spaced apart sheets 134, 136 of one of the above-referenced separator materials, for example sheets of microporous, polyolefinic film, are connected to a polymeric ring 138. The separator sheets 134 and 136 are disposed intermediate the anode 102 and the coated sidewalls 110 and 112, respectively, serving as the cathode 104. The microporous structure provides for ion flow therethrough during charge and discharge cycles while the polymeric ring 138 frames the sheets 134, 136 to provide structural support for them. Alternatively, the polymeric ring can be eliminated and the separator sheets 134, 136 are sealed to each other in a known manner at their peripheries to envelope the anode 102.

Figure 9:
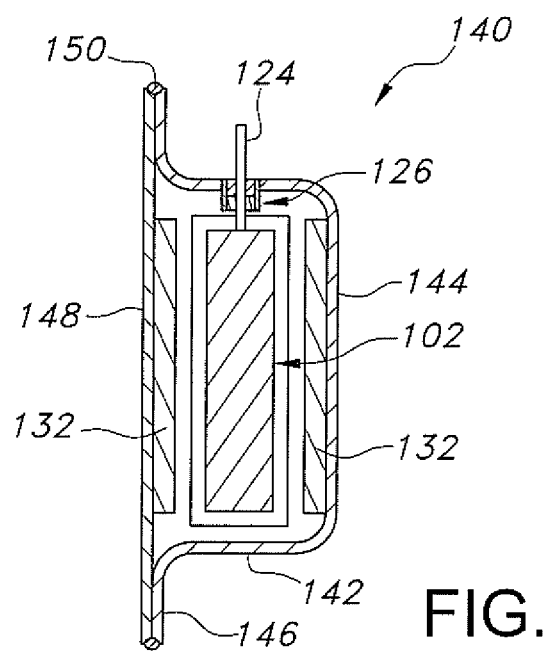
FIGS. 9 and 10 are elevational, cross-sectional views of various alternate embodiments of capacitors 140 and 152, respectively, according to the present invention.

FIG. 9 shows another embodiment of a capacitor 140 according to the present invention. Capacitor 140 has electrode active material 132 selectively contacted to a substrate provided in the shape of a contoured cup having an annular sidewall 142 extending from a contoured bottom wall 144. The annular sidewall 142 forms into a contoured annular rim 146. The rim 146 is connected to a contoured lid 148 by weld 150 to complete the enclosure. The bottom wall 144, annular rim 146 and lid 148 are contoured according to a desired one of the various casing sidewall shapes described above with respect to FIGS. 3 to 5.

Figure 10:
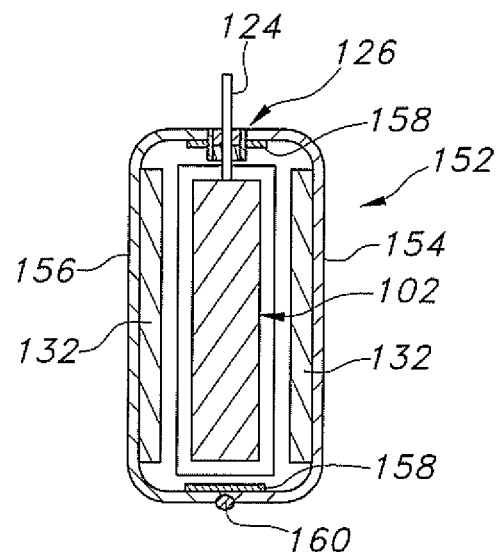

FIG. 10 shows another embodiment of a capacitor 152 according to the present invention. Capacitor 152 is comprised of contoured tray-shaped or clam-shell type members 154 and 156 having annular edges that are butted together and connected by a weld 160. An annular back-up ring 158 fits inside the contoured sidewall portions of the trays 154, 156 to provide support when the trays are connected along their butted edges by the weld 160. The electrode active material 132 is selectively contacted to the contoured major sidewalls 154A and 156A of the respective tray-shaped members 154 and 156. The major sidewalls 154A and 156A are contoured according to a desired one of the various casing sidewall shapes described above with respect to FIGS. 3 to 5.

Figure 11A:
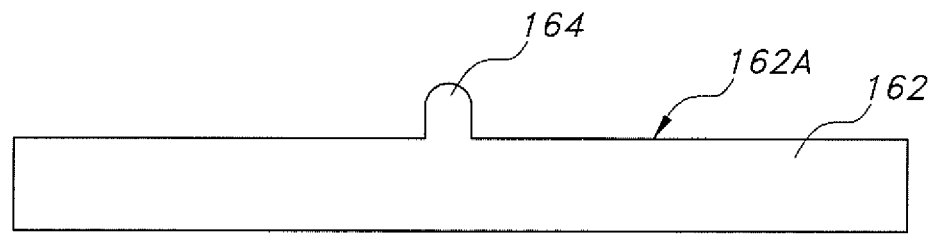
FIGS. 11A to 11C are side-elevational views of fixtures 162, 166 and 170, respectively, for pressing valve metal pellets that are suitable for being bent into contoured shapes so that the pellets can be housed in the casings illustrated in FIGS. 3 to 10.
Figure 11B:
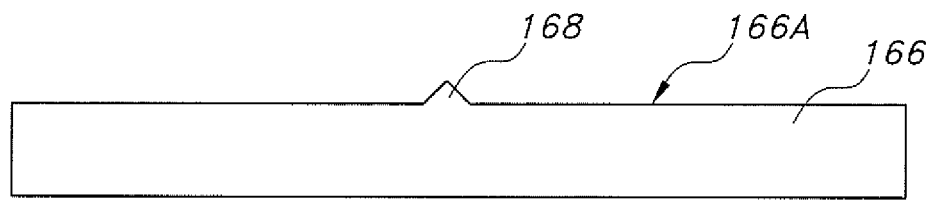
Figure 11C:
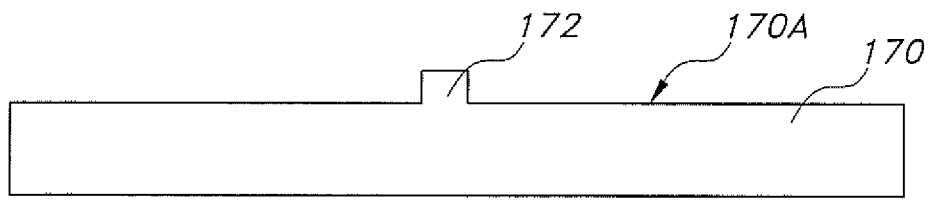

Referring now to FIGS. 11A to 11C, various fixtures are shown for forming the pressed anode pellet 12 illustrated in FIGS. 1, 1A and 2. The pressing fixture illustrated in FIG. 11A comprises a plate 162 having a substantially planar working surface 162A from which an elongate U-shaped protrusion 164 extends. Likewise, the pressing fixture illustrated in FIG. 11B comprises a plate 166 having a substantially planar working surface 166A from which an elongate V-shaped protrusion 168 extends. Similarly, the pressing fixture illustrated in FIG. 11C comprises a plate 170 having a substantially planar working surface 170A from which an elongate rectangular-shaped protrusion 172 extends.

As previously discussed, the anode pellet 12 illustrated in FIGS. 1, 1A and 2 is made from a flowable valve metal powder, for example, tantalum powder, that has been pressed into a desired shape. An exemplary pressing fixture comprises a cup-shaped lower fixture (not shown) having either an elongate U-shaped protrusion 164, an elongate V-shaped protrusion 168 or an elongate rectangular-shaped protrusion 172, as shown with respect to the plates 162, 166 and 170 illustrated in FIGS. 11A to 11C, extending upwardly from a planar working surface. A quantity of tantalum powder is flowed into the lower fixture to fill the lower fixture about half full. After an anode lead wire 20 is positioned on top of the tantalum powder, a second quantity of tantalum powder is flowed into the lower fixture. The upper fixture plate having the matching U-shaped protrusion 164, V-shaped protrusion 168 or rectangular-shaped protrusion 172 is positioned on top of the tantalum powder filling the lower fixture, and the upper plate is pressed downwardly to compress the tantalum powder in a pellet. The thusly formed pressed tantalum pellet, for example, the pellet 12 shown in FIG. 1 has the first and second U-shaped recesses 22, 24 aligned front-to-back with each other and extending inwardly part-way into the thickness of the presses anode pellet to intersect the embedded lead wire portion 20A. The pressed anode pellet is then bent into a suitable configuration at the recesses 22, 24 so that it can be housed in one of the exemplary casings illustrated in FIGS. 3 to 5.

Figure 12:
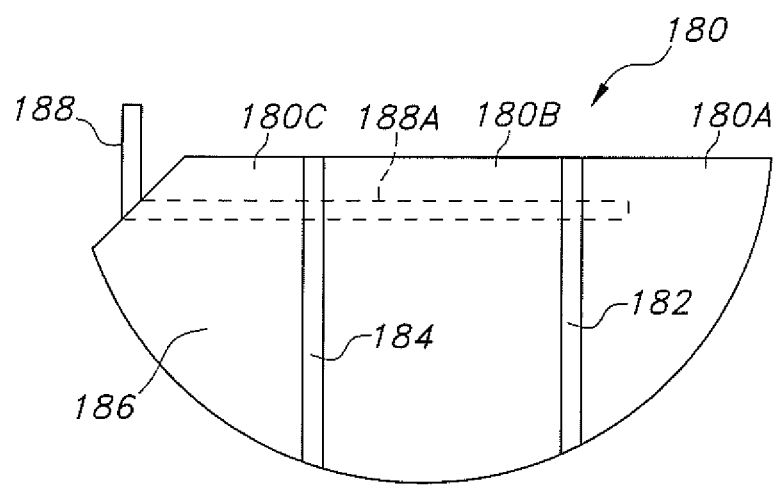
FIG. 12 is a side elevational view of a pressed valve metal pellet 180 with spaced-apart channel-shaped recesses 182 and 184 according to the present invention.
Figure 12A:
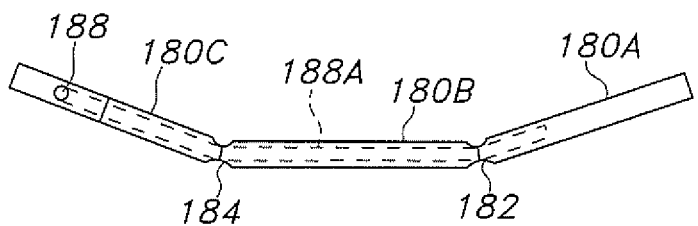
FIG. 12A is a plan view looking down at the upper edge of the pressed pellet 180 shown in FIG. 12 after having been bent at the channel-shaped recesses 182 and 184.

FIGS. 12 and 12A illustrate another embodiment of a valve metal anode 180, for example, of a pressed tantalum pellet, according to the present invention. The pressed tantalum pellet has side-by-side channel-shaped recesses 182 and 184 that extend inwardly from a front major face wall 186 to intersect with the embedded portion 188A of an anode lead wire 188 and that extend to opposed locations at the surrounding peripheral edge of the pressed pellet. While not shown in the drawing, the opposed back major face wall is likewise provided with side-by-side channel-shaped recesses that extend inwardly to intersect the embedded lead wire portion 188A and that extend to opposed locations at the surrounding peripheral edge of the pressed pellet. The side-by-side channel-shaped recesses extending inwardly from the front and back major face walls are aligned front-to-back with each other. This enables the pressed pellet to be bent into a configuration having a right pellet portion 180A, an intermediate pellet portion 180B and a left pellet portion 180C aligned at acute angles with respect to each other. The embedded lead wire portion 188A keeps the right, intermediate and left pellet portions 180A, 180B and 180C connected to each other and ensures that there is electrical continuity between them to the extending lead wire portion 188A.

Figure 13:
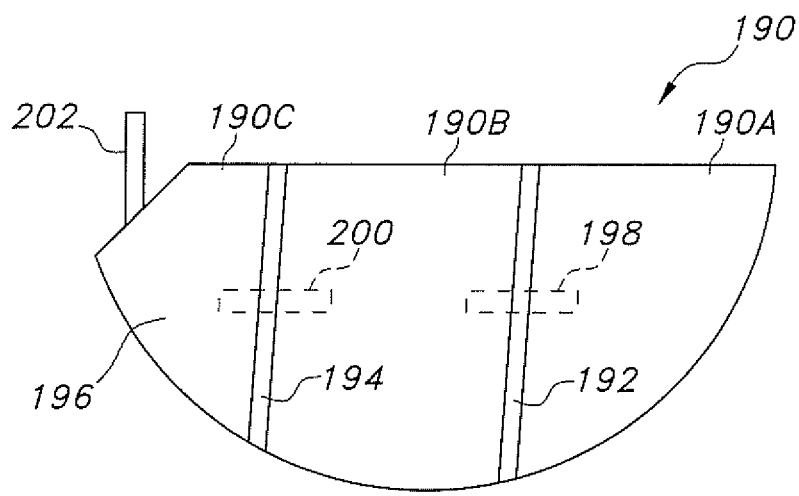
FIG. 13 is a side elevational view of another embodiment of a pressed valve metal pellet 190 with spaced-apart channel-shaped recesses 192 and 194 according to the present invention.

FIG. 13 illustrates another embodiment of a valve metal anode 190, for example, of a pressed tantalum pellet, according to the present invention. The pressed tantalum pellet has side-by-side channel-shaped recesses 192 and 194 that extend inwardly from a front major face wall 196 to intersect with embedded wires 198 and 200 and that extend to opposed locations at the surrounding peripheral edge of the pressed pellet. While not shown in the drawing, the opposed back major face wall is likewise provided with side-by-side channel-shaped recesses that extend inwardly to intersect the embedded wires 198 and 200 and that extend to opposed locations at the surrounding peripheral edge of the pressed pellet. The side-by-side channel-shaped recesses extending inwardly from the front and back major face walls are aligned front-to-back with each other. Unlike the embedded lead wire 20 shown in FIGS. 1, 1A and 2 and the lead wire 188 shown in FIGS. 12 and 12A, however, the embedded wires 198 and 200 in this pressed pellet are not connected to the extending lead wire 202. Nonetheless, the embedded wires 198 and 200 enable the pressed pellet to be bent into a configuration having a right pellet portion 190A, an intermediate pellet portion 190B and a left pellet portion 190C. The right, intermediate and left anode pellet portions 190A, 190B and 190C are at acute angles with respect to each other. The embedded wires 198 and 200 keep the right, intermediate and left pellet portions 190A, 190B and 190C connected to each other and ensure that there is electrical continuity between them to the extending lead wire 202.

Figure 14:
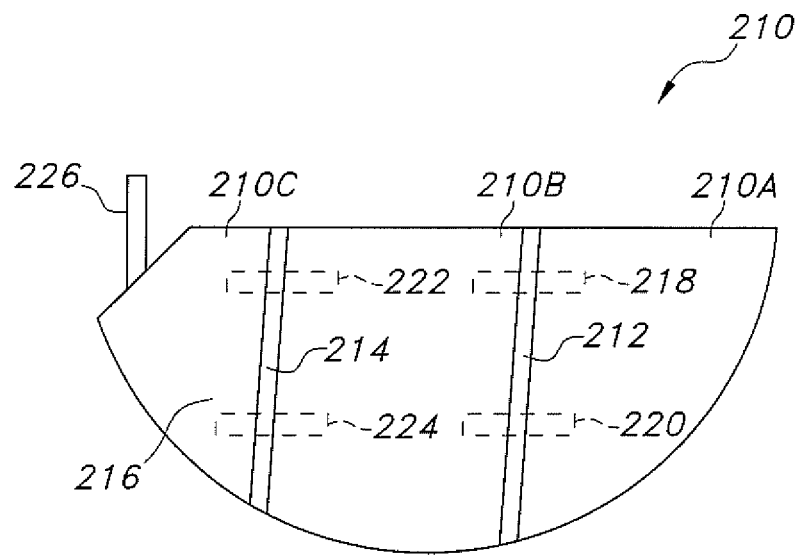
FIG. 14 is a side elevational view of another embodiment of a pressed valve metal pellet 210 with spaced-apart channel-shaped recesses 212 and 214 according to the present invention.

FIG. 14 illustrates another embodiment of a valve metal anode 210, for example, of a pressed tantalum pellet, according to the present invention. The pressed tantalum pellet has side-by-side channel-shaped recesses 212 and 214 that extend inwardly from a front major face wall 216 to intersect with embedded wires 218, 220, 222 and 224 and that extend to opposed locations at the surrounding peripheral edge of the pressed pellet. While not shown in the drawing, the opposed back major face wall is likewise provided with side-by-side channel-shaped recesses that extend inwardly to intersect the embedded wires 218, 220, 222 and 224 and that extend to opposed locations at the surrounding peripheral edge of the pressed pellet. The side-by-side channel-shaped recesses extending inwardly from the front and back major face walls are aligned front-to-back with each other. More particularly, channel-shaped recess 212 intersects spaced-apart wires 218 and 220 at a right-angle or normal orientation. Likewise, channel-shaped recess 214 intersects spaced-apart wires 222 and 224 at a right-angle orientation.

In a similar manner as with the embedded wires 198 and 200 shown in the anode 190 illustrated in FIG. 13, the embedded wires 218, 220, 222 and 224 are not connected to the extending lead wire 226. Nonetheless, the embedded wires 218, 220, 222 and 224 enable the presses pellet to be bent into a configuration having a right pellet portion 210A, an intermediate pellet portion 210B and a left pellet portion 210C. The right, intermediate and left anode pellet portions 210A, 210B and 210C are at acute angles with respect to each other. The embedded wires 218, 220, 222 and 224 keep the right, intermediate and left pellet portions 210A, 210B and 210C connected to each other and ensure that there is electrical continuity between them to the extending lead wire 226.

Figure 15:
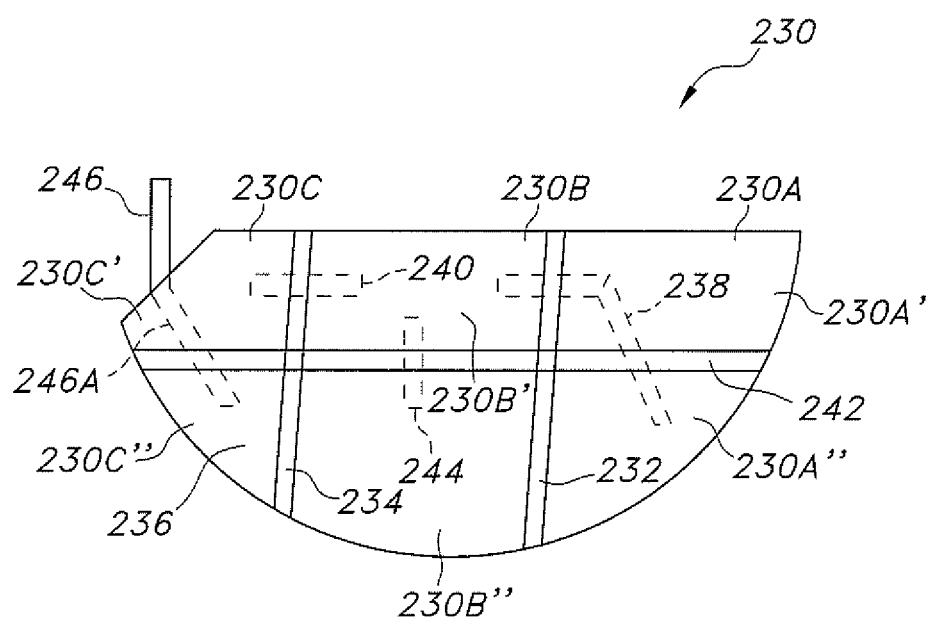
FIG. 15 is a side elevational view of another embodiment of a pressed valve metal pellet 230 with spaced-apart channel-shaped recesses 232 and 234 and a lateral channel-shaped recess 242 that intersects the recesses 232, 234 according to the present invention.

FIG. 15 illustrates another embodiment of a valve metal anode 230, for example, of a pressed tantalum pellet, according to the present invention. The pressed tantalum pellet has side-by-side channel-shaped recesses 232 and 234 that extend inwardly from a front major face wall 236 to intersect with embedded wires 238 and 240 and that extend to opposed locations at the surrounding peripheral edge of the pressed pellet. While not shown in the drawing, the opposed back major face wall is likewise provided with side-by-side channel-shaped recesses that extend inwardly to intersect the embedded wires 238 and 240 and that extend to opposed locations at the surrounding peripheral edge of the pressed pellet. The side-by-side channel-shaped recesses extending inwardly from the front and back major face walls are aligned front-to-back with each other.

As is the case with the anode 10 shown in FIGS. 1, 1A and 2, the anode 180 shown in FIGS. 12 and 12A, the anode 190 shown in FIG. 13 and the anode 210 shown in FIG. 14, the channel-shaped recesses 238 and 240, which are aligned substantially parallel to each other, extend to opposed locations at the surrounding peripheral edge of the pressed pellet.

Further, this valve metal anode 230 has a third or lateral-extending channel-shaped recess 242 that intersects recesses 232 and 234. Channel-shaped recess 242 is shown intersecting the channel-shaped recesses 232 and 234 at a right angle, but that is not necessary. It is only important that the lateral channel-shaped recess 242 intersects the two channel-shaped recesses 232 and 234 and extends to opposed locations at the surrounding peripheral edge of the pressed pellet. The lateral-extending channel-shaped recess 242 intersects the embedded wire 238, which is also intersected by the channel-shaped recess 232, a third embedded wire 244 and the embedded portion 246A of the lead wire 246. Further, channel-shaped recess 232 intersects embedded wire 238 at a right angle or normal orientation. Likewise, channel-shaped recess 234 intersects embedded wire 240 at a right-angle orientation.

In a similar manner as with the embedded wires 198 and 200 shown in the pressed pellet 190 illustrated in FIG. 13 and the embedded wires 218, 220, 222 and 224 shown in the pressed pellet 201 illustrated in FIG. 14, the embedded wires 238, 240 and 244 are not connected to the extending lead wire 246. Nonetheless, the embedded wires 238, 240 and 244 and the embedded portion 246A of the lead wire 246 enable the presses pellet to be bent along channel-shaped recesses 232 and 234 into a configuration having a right pellet portion 230A, an intermediate pellet portion 230B and a left pellet portion 230C. The right, intermediate and left anode pellet portions 230A, 230B and 230C are at acute angles with respect to each other. The embedded wires 238, 240 and 244 and the embedded portion 246A of the lead wire 246 keep the right, intermediate and left pellet portions connected to each other to ensure that there is electrical continuity between them to the extending lead wire 246. Moreover, the channel-shaped recess 242 allows pellet portion 230A to be bent into sub-portions 230A', 230A", pellet portion 230B to be bent into sub-portions 230B', 230B", and pellet portion 230C to be bent into sub-portions 230C', 230C" while ensuring that there is electrical continuity between the sub-portions to the extending lead wire 246.

Thus, various casing configurations for implantable capacitors are described where the casing has a contoured shape that more closely matches the anatomical shape of a human than traditional prismatic and mating clam-shell type casings. Since the capacitor casing is contoured, the present invention further describes various valve metal anode configurations that are shaped to match the contoured casing. That way, an anatomically-shaped capacitor is shown and described where the internal volume of the casing is occupied with anode and cathode active materials to provide a capacitor that is volumetrically efficient.

Although several embodiments of the present invention have been described in detail, that is for purposes of illustration. Various modifications of each embodiment may be made without departing from the spirit and scope of the present invention. Accordingly, the present invention is not to be limited, except as by the appended claims.

What is claimed is:

1. An anode for a capacitor, the anode comprising:
    a) an anode pellet of an anode active material comprising a surrounding peripheral edge extending to a first major face wall spaced from and opposed to a second major face wall;
    b) an anode lead wire comprising an embedded anode lead wire portion and an extending anode lead wire portion, wherein the embedded anode lead wire portion extends into the anode pellet between the first and second major face walls, and wherein the extending anode lead wire portion extends outwardly from the surrounding peripheral edge of the anode pellet;
    c) a first channel-shaped recess extending into the anode pellet from the first major face wall to intersect with the embedded anode lead wire portion, wherein the first channel-shaped recess extends to opposed locations at the surrounding peripheral edge of the anode pellet; and
    d) a second channel-shaped recess extending into the anode pellet from the second major face wall to intersect with the embedded anode lead wire portion, wherein the second channel-shaped recess extends to opposed locations at the surrounding peripheral edge of the anode pellet, and e) wherein the first and second channel-shaped recesses are aligned front-to-back with each other.

2. The anode of claim 1, wherein the anode pellet is bent at the aligned first and second channel- shaped recesses intersecting the embedded anode lead wire portion and extending to the opposed locations at the surrounding peripheral edge of the anode pellet to thereby provide a right anode pellet portion electrically connected to a left anode pellet portion by the embedded anode lead wire portion.

3. The anode of claim 2, wherein the right and left anode pellet portions are at an acute angle with respect to each other.

4. The anode of claim 1, wherein the aligned first and second channel-shaped recesses comprise a first pair of aligned channel-shaped recesses, and wherein the anode pellet comprises a spaced-apart second pair of aligned channel-shaped recesses extending inwardly from the front and back major face walls respectively to intersect the embedded anode lead wire portion, the second pair of aligned channel-shaped recesses extending to opposed locations at the surrounding peripheral edge of the anode pellet.

5. The anode of claim 4, wherein the anode pellet is bent at the first pair of aligned channel-shaped recesses and at the second pair of aligned channel-shaped recesses to thereby provide a right anode pellet portion electrically connected to an intermediate anode pellet portion electrically connected to a left anode pellet portion by the embedded anode lead wire portion.

6. The anode of claim 5, wherein the anode pellet is bent at the first pair of aligned channel-shaped recesses and at the second pair of aligned channel-shaped recesses to thereby provide a right anode pellet portion electrically connected to an intermediate anode pellet portion by the embedded wire with the intermediate anode pellet portion being electrically connected to a left anode pellet portion by the embedded anode lead wire portion.

7. The anode of claim 1, wherein the anode pellet has an embedded wire that is not directly connected to the embedded anode lead wire portion, and wherein the first and second channel-shaped recesses comprise a first pair of aligned channel-shaped recesses intersecting the embedded anode lead wire portion and extending to the opposed locations at the surrounding peripheral edge of the anode pellet, and wherein the anode pellet comprises a spaced-apart second pair of aligned channel-shaped recesses extending inwardly from the front and back major face walls respectively to intersect the embedded wire, the second pair of channel-shaped recesses extending to opposed locations at the surrounding peripheral edge of the anode pellet.

8. The anode of claim 1, wherein the anode pellet is of a valve metal selected from the group of tantalum, aluminum, niobium, or titanium.

9. The anode of claim 1, wherein the first and second channel-shaped recesses have a cross-sectional shape selected from a U-shaped cross-section, a V-shaped cross-section, and a rectangular-shaped cross-section.

10. An anode for a capacitor, the anode comprising:
    a) an anode pellet of an anode active material comprising a surrounding peripheral edge extending to a first major face wall spaced from and opposed to a second major face wall;
    b) an anode lead wire extending outwardly from the surrounding peripheral edge of the anode pellet;
    c) a first embedded wire that resides in the anode pellet between the first and second major face walls;
    d) a first channel-shaped recess extending into the anode pellet from the first major face wall to intersect with the first embedded wire, wherein the first channel-shaped recess extends to opposed locations at the surrounding peripheral edge of the anode pellet; and
    e) a second channel-shaped recess extending into the anode pellet from the second major face wall to intersect with the first embedded wire, wherein the second channel-shaped recess extends to opposed locations at the surrounding peripheral edge of the anode pellet, and
    f) wherein the first and second channel-shaped recesses are aligned front-to-back with each other.

11. The anode of claim 10, wherein the first embedded wire is not directly connected to the anode lead wire.

12. The anode of claim 10, further comprising a second embedded wire residing in the anode pellet between the first and second major face walls, wherein the first and second channel-shaped recesses comprise a first pair of aligned channel-shaped recesses, and wherein the anode pellet comprises a spaced-apart second pair of aligned channel-shaped recesses extending inwardly from the front and back major face walls respectively to intersect the second embedded wire, the second pair of aligned channel-shaped recesses extending to opposed locations at the surrounding peripheral edge of the anode pellet, and wherein the first and second embedded wires are not directly connected to each other or to the anode lead wire.

13. The anode of claim 12, wherein the anode pellet is bent at the first pair of aligned channel-shaped recesses and at the second pair of aligned channel-shaped recesses to thereby provide a right anode pellet portion electrically connected to an intermediate anode pellet portion by the first embedded wire, the intermediate anode pellet portion being electrically connected to a left anode pellet portion by the second embedded wire.

14. The anode of claim 13, wherein the anode lead wire comprises an embedded anode lead wire portion and an extending anode lead wire portion, the embedded anode lead wire portion extending into the anode pellet between the first and second major face walls, and wherein the first and second pairs of aligned channel-shaped recesses do not intersect with the embedded anode lead wire portion and the extending anode lead wire portion extends outwardly from the surrounding peripheral edge of the anode pellet.

15. The anode of claim 10, further comprising:
a) a second embedded wire and a third embedded wire, both the second and third embedded wires residing in the anode pellet between the first and second major face walls,
b) wherein the first and second channel-shaped recesses comprise a first pair of aligned channel-shaped recesses, and wherein the anode pellet comprises a second pair of aligned channel-shaped recesses extending inwardly from the front and back major face walls respectively to intersect the second embedded wire and the third embedded wire, the second pair of aligned channel-shaped recesses extending to opposed locations at the surrounding peripheral edge of the anode pellet, and wherein the first and second pairs of aligned channel-shaped recesses intersect with each other, and
c) wherein the anode pellet is bent at the first pair of aligned channel-shaped recesses to thereby provide a right anode pellet portion electrically connected to a left anode pellet portion by the first embedded wire, and
d) wherein the anode pellet is further bent at the second pair of aligned channel-shaped recesses to thereby provide the right anode pellet portion comprising upper and lower right anode sub-portions electrically connected to each other by the second embedded wire and to provide the left anode pellet portion comprising upper and lower left anode sub-portions electrically connected to each other by the third embedded wire.

16. The anode of claim 15, wherein the first and second embedded wires are not directly connected to each other or to the anode lead wire.

17. A capacitor, comprising:
a) a casing comprising spaced apart first and second major sidewalls extending to and meeting with opposed third and fourth end walls, the first and second major sidewalls and the third and fourth end walls extending from a bottom wall to an open end closed by a lid, wherein the first and second major sidewalls are curved in a similar direction; and
b) an electrode assembly housed inside the casing, the electrode assembly comprising a separator disposed between an anode and a cathode, the anode comprising:
  i) an anode pellet of an anode active material comprising a surrounding peripheral edge extending to a first major face wall spaced from and opposed to a second major face wall;
  ii) an anode lead wire comprising an embedded anode lead wire portion and an extending anode lead wire portion, wherein the embedded anode lead wire portion extends into the anode pellet between the first and second major face walls, and wherein the extending anode lead wire portion extends outwardly from the surrounding peripheral edge of the anode pellet;
  iii) a first channel-shaped recess extending into the anode pellet from the first major face wall to intersect with the embedded anode lead wire portion, wherein the first channel-shaped recess extends to opposed locations at the surrounding peripheral edge of the anode pellet; and
  iv) a second channel-shaped recess extending into the anode pellet from the second major face wall to intersect with the embedded anode lead wire portion, wherein the second channel-shaped recess extends to opposed locations at the surrounding peripheral edge of the anode pellet, and wherein the first and second channel-shaped recesses are aligned front-to-back with each other,
  v) wherein the anode pellet is bent at the aligned first and second channel-shaped recesses intersecting the embedded anode lead wire portion to thereby provide a right anode pellet portion electrically connected to a left anode pellet portion by the embedded anode lead wire portion with the right and left anode pellet portions having a shape that matches the curve of the casing, and
c) a working electrolyte provided in the casing in contact with the anode and the cathode.

18. The capacitor of claim 17, wherein the casing is of a material selected from the group of nickel, aluminum, stainless steel, mild steel, tantalum, and titanium.

19. The capacitor of claim 17, wherein the bottom wall of the casing is either planar or curved.

20. The capacitor of claim 17, wherein the casing is of either mating clam-shell type members or of a contoured cup closed by a contoured lid.

* * * * *

UNITED STATES PATENT AND TRADEMARK OFFICE
CERTIFICATE OF CORRECTION

PATENT NO. : 11,217,397 B2
APPLICATION NO. : 17/151258
DATED : January 4, 2022
INVENTOR(S) : Jason T. Hahl et al.

It is certified that error appears in the above-identified patent and that said Letters Patent is hereby corrected as shown below:

In the Claims

Column 11, Line 34 (Claim 1, Lines 34-36) after the word "and" delete "e) wherein the first and second channel-shaped recesses are aligned front-to-back with each other" and insert the same at Line 35 of Column 11

Column 11, Line 38 (Claim 2, Line 2) delete "channel- shaped" and insert --channel-shaped--

Column 12, Line 43 (Claim 10, Line 20) delete "f) wherein the first and second channel-shaped recesses are aligned front-to-back with each other." and insert to align with indents of a) through e)

Column 14, Lines 12 through 37 (Claim 17, Lines 16-43) after the end of the text of item "i" delete all of the text for items "ii), iii), iv), and v)" and insert all items --ii), iii), iv), and v)-- and their respective texts to align to the indents of i)

Signed and Sealed this
Twenty-first Day of February, 2023

Katherine Kelly Vidal
*Director of the United States Patent and Trademark Office*